United States Patent
Ohtani et al.

(10) Patent No.: US 8,252,311 B2
(45) Date of Patent: Aug. 28, 2012

(54) BONE STRENGTHENING FOOD SUPPLEMENT

(75) Inventors: Junji Ohtani, Hiroshima (JP); Ikuko Ishikawa, Hiroshima (JP)

(73) Assignee: Ishikawa Co., Ltd., Hiroshima-Shi, Hiroshima (JP)

( * ) Notice: Subject to any disclaimer, the term of this patent is extended or adjusted under 35 U.S.C. 154(b) by 248 days.

(21) Appl. No.: 12/673,577

(22) PCT Filed: Apr. 27, 2009

(86) PCT No.: PCT/JP2009/001923
§ 371 (c)(1),
(2), (4) Date: Feb. 15, 2010

(87) PCT Pub. No.: WO2009/133694
PCT Pub. Date: Nov. 5, 2009

(65) Prior Publication Data
US 2011/0104237 A1    May 5, 2011

(30) Foreign Application Priority Data
May 2, 2008 (JP) ................................ 2008-120307

(51) Int. Cl.
*A61K 47/00* (2006.01)
(52) U.S. Cl. .............................. 424/439; 426/93; 426/94
(58) Field of Classification Search .................. 424/439; 426/93, 94
See application file for complete search history.

(56) References Cited

U.S. PATENT DOCUMENTS
2004/0013656 A1 * 1/2004 Matsubara et al. ......... 424/93.45

FOREIGN PATENT DOCUMENTS

| | | |
|---|---|---|
| JP | 6-46797 A | 2/1994 |
| JP | 11-113532 A | 4/1999 |
| JP | 2003-33158 A | 2/2003 |
| JP | 2004-121060 A | 4/2004 |
| JP | 2007-195529 A | 8/2007 |
| JP | 2008-35730 A | 2/2008 |

OTHER PUBLICATIONS

Miyauchi, A. et al., "Novel Ipriflavone Receptors Coupled to Calcium Influx Regulate Osteoclast Differentiation and Function", Endocrinology, (1996), vol. 137, pp. 3544-3550.
Mora-Gutierrez, A. et al., "Influence of bovine and caprine casein phosphopeptides differing in alphas1-casein content in determining the absorption of calcium from bovine and caprine calcium-fortified milks in rats", Journal of Dairy Research, (2007), vol. 74, pp. 356-366.
Kudou, S. et al., "Malonyl Isoflavone Glycosides in Soybean Seeds (Glycine max MERRILL)", Agric. Biol. Chem., vol. 55, pp. 2227-2233, (1991).
International Search Report for PCT/JP2009/001923 mailed Aug. 11, 2009.

* cited by examiner

*Primary Examiner* — Rebecca Prouty
*Assistant Examiner* — Danielle Sullivan
(74) *Attorney, Agent, or Firm* — Roberts Mlotkowski Safran & Cole P.C.

(57) ABSTRACT

Black beans B are coated with a mineral layer 1 containing calcium powder and dolomite powder, a dough layer 2 formed by roasting a dough mixture containing flour, and an outside layer 3 formed by solidifying a seasoning mixture containing, for example, soymilk powder and powdered tea with hardened fat or oil. In 30 parts by weight of black beans, from 2 to 5, both inclusive, parts by weight of the calcium powder, from 30 to 45, both inclusive, parts by weight of the dolomite powder, and from 5 to 15, both inclusive, parts by weight of the soymilk powder, are contained.

6 Claims, 9 Drawing Sheets

| | EXAMPLE 1 | EXAMPLE 2 | EXAMPLE 3 | EXAMPLE 4 | EXAMPLE 5 |
|---|---|---|---|---|---|
| BLACK BEANS | 30 | 30 | 30 | 30 | 30 |
| CALCIUM POWDER | 2.8 | 2.8 | 2.5 | 2.5 | 2.5 |
| DOLOMITE POWDER | 38 | 38 | 38 | 38 | 38 |
| SOYMILK POWDER | 13 | 10 | 13 | 11 | 9 |
| MILK POWDER | 26 | 20 | 26 | 22 | 18 |
| POWDERED TEA | 35 | 28 | | | 25 |
| CPP | | 4 | | 3 | 3 |
| LEMON PEEL POWDER | | | 27 | 27 | 13 |

FIG.5A TOTAL BONE DENSITY (FEMALE)

FIG.5B TOTAL BONE MINERAL DENSITY (FEMALE)

BONE STRENGTHENING FOOD SUPPLEMENT

TECHNICAL FIELD

The present invention relates to bone strengthening food supplements which enable effective absorption of calcium in the body, and thus are useful for preventing the onset of osteoporosis and maintaining or improving bone conditions.

BACKGROUND ART

Calcium is a major component of bones, but is often in short supply in daily diet. Therefore, problems such as osteoporosis, e.g., a decrease in bone mass due to a reduced bone density and a considerable decrease in bone strength, can arise.

In view of this, there has been a demand for means for enabling an easy intake of an appropriate amount of calcium. As such means, calcium-containing mamegashi (a confection made by coating beans with wheat, sugar, or other materials) is proposed (see, PATENT DOCUMENT 1).

Mamegashi is generally produced by attaching layers of kanbai-ko (a type of glutinous rice flour) and/or wheat to, for example, soybeans with syrup, roasting the soybeans, and then seasoning the soybeans (see, for example, PATENT DOCUMENT 2). Specifically, in this process, the surfaces of the soybeans are coated with syrup mixed with milk calcium, then wheat flour or glutinous rice flour is attached to these surfaces to form layers, and then the soybeans are roasted. After the roasting, the soybeans are further coated with cocoa by using syrup, and then the soybeans are dried.

In this manner, coating the strong-tasting milk calcium with layers of flour, cocoa, or other materials enables an easy intake of calcium.

Calcium is preferably taken together with magnesium, and the calcium:magnesium ratio is preferably 2:1.

CITATION LIST

Patent Document

PATENT DOCUMENT 1: Japanese Patent Publication No. 2004-121060
PATENT DOCUMENT 2: Japanese Patent Publication No. 2007-195529

SUMMARY OF THE INVENTION

Technical Problem

Calcium is poorly absorbed in the body. Accordingly, even when calcium is taken in the body, only addition of calcium, as described in mamegashi of PATENT DOCUMENT 1, might fail to fully utilize calcium, or rather, might disturb mineral balance to adversely affect the body.

In particular, in such a case as the onset of osteoporosis, bone metabolism disorder has occurred. Thus, unless the bone metabolism is recovered from the disorder, it is difficult to achieve sufficient improvement only with an intake of a large amount of calcium.

It is therefore an object of the present invention to provide bone strengthening food supplements. The bone strengthening food supplements enable an easy intake of calcium, which is often in short supply in daily diet, while obtaining good taste, are excellent in mineral balance, provide efficient absorption of calcium in the body, and effectively increase bone density to be also useful for improvement of osteoporosis.

Solution to the Problem

To achieve the object, the inventors of the present invention selected various materials which are considered to effectively increase bone density, and intensively studied combinations and proportions of materials, to find out given proportions of soybeans, calcium powder, dolomite powder, and soymilk powder in a mixture mainly made of these materials.

Specifically, a bone strengthening food supplement according to the present invention includes: from 2 to 5, both inclusive, parts by weight of calcium powder per 30 parts by weight of soybeans; from 30 to 45, both inclusive, parts by weight of dolomite powder per 30 parts by weight of the soybeans; and from 5 to 15, both inclusive, parts by weight of soymilk powder per 30 parts by weight of the soybeans.

As will be specifically described later, it was verified that this bone strengthening food supplement provides significant advantages in increasing bone density, especially in improving osteoporosis.

These advantages are considered to be because of the following reasons. Soybeans and soymilk powder are rich in isoflavone, which effectively reduces osteoporosis. In addition, mixture of calcium powder and dolomite powder in the above-mentioned proportions allows the ratio of calcium and magnesium to be approximately 2:1 where excellent mineral balance can be obtained. Accordingly, the bone metabolism is well balanced, resulting in promoting absorption of calcium, and thereby, increasing bone density.

Further, the bone strengthening food supplement preferably further includes from 10 to 40, both inclusive, parts by weight of milk powder. In this case, since milk powder contains lactose, which promotes absorption of calcium, the increase in bone density can be ensured.

Furthermore, the supplement preferably includes powdered tea. In this case, the flavor of powdered tea can mask flavors of calcium and dolomite, thereby enhancing the taste of the supplement. In addition, since powdered tea contains catechin, the advantages of controlling a blood-pressure rise and adjusting blood glucose levels can be achieved.

The supplement may further include citrus calcium. Citrus calcium herein is calcium contained in citruses. Peels of citruses, for example, contain relatively large amounts of calcium, and thus powder, grains, chips, and the like containing citrus calcium may substitute the calcium powder. Citrus calcium can be used as a sour seasoning in itself, and thus can make the supplement easy to eat.

To enhance absorption of calcium, the supplement may further include from 1 to 4, both inclusive, parts by weight of casein phosphopeptide (also simply referred to as CPP). In this case, calcium can be more stably absorbed in the body without deterioration of flavor, thereby ensuring an increase in bone density.

In addition to CPP, materials such as fructo-oligosaccharide, calcium citrate-malate, poly glutamic acid, calcium hydrogenphosphate, phosphoryl oligosaccharide calcium, dibasic calcium phosphate, and casein phosphopeptide—amorphous calcium phosphate (CPP-ACP), may be contained in the supplement. Then, absorption of calcium can be further promoted.

As a specific example, the bone strengthening food supplement with the composition described above, may be formed in the form of mamegashi, for example.

Specifically, the bone strengthening food supplement may include a plurality of layers covering each of the soybeans and including: a first layer containing the calcium powder and the dolomite powder and formed on an outside of each of the soybeans; a second layer formed on an outside of the first layer by roasting a dough mixture containing flour; a third layer formed on an outside of the second layer by solidifying a seasoning mixture containing the soymilk powder with fat or oil which is hardened at room temperature (also referred to as hardened fat or oil).

The bone strengthening food supplement with the above structure is easy to eat, and enables a calcium intake to be calculated on the basis of number of soybeans. Accordingly, even elderly people and children can take appropriate amounts of calcium without a mistake.

In the supplement, the innermost layer is a layer of calcium and dolomite powder which is not easy to eat and has a relatively hard texture. This innermost layer is covered with a second layer which is relatively soft and has crispy texture. The second layer is covered with a third layer solidified with hardened fat or oil and having an appropriate hardness. In this manner, the supplement can be chewed with a comfortable texture, and even elderly people having reduced chewing force can eat the supplement without feeling uncomfortable with hardness. In addition, advantageously, strong flavor can be masked with the seasoning mixture in the third layer.

In particular, when the supplement is placed in the mouth, hardened fat or oil is softened by heat of the body, and the thus the seasoning mixture powder is melt, thereby exhibiting a higher masking effect. Further, the hardened fat or oil can prevent moisture from being absorbed in the first and second layers, thereby stably maintaining different textures.

In this case, a cereal flour layer is preferably formed between the first layer and each of the soybeans. Then, the first layer is stably formed on the outside of the soybeans, thereby enabling stable mass production of high-quality bone strengthening food supplements.

Further, a starch layer is preferably formed between the second layer and the third layer. In this case, the third layer can be stably formed on the outside of the second layer, thereby enabling stable mass production of higher-quality bone strengthening food supplements.

ADVANTAGES OF THE INVENTION

As described above, the present invention provides bone strengthening food supplements which are easy to eat with good taste, show excellent mineral balance, can effectively increase bone density, and are useful for preventing the onset of osteoporosis and maintaining or improving bone conditions.

BRIEF DESCRIPTION OF THE DRAWINGS

FIGS. 4(a) and 4(b) are graphs showing results of verification experiments performed on male mice.

FIGS. 5(a) and 5(b) are graphs showing results of verification experiments performed on female mice.

FIGS. 6(a) and 6(b) are graphs showing results of verification experiments performed on male mice.

FIGS. 7(a) and 7(b) are graphs showing results of verification experiments performed on female mice.

FIGS. 8(a) and 8(b) are graphs showing results of verification experiments performed on male mice.

FIGS. 9(a) and 9(b) are graphs showing results of verification experiments performed on female mice.

DESCRIPTION OF EMBODIMENTS

An embodiment of the present invention will be described in detail hereinafter with reference to the drawings. The following embodiment is merely an example in nature, and is not intended to limit the scope, applications, and use of the invention.

Figure 1:
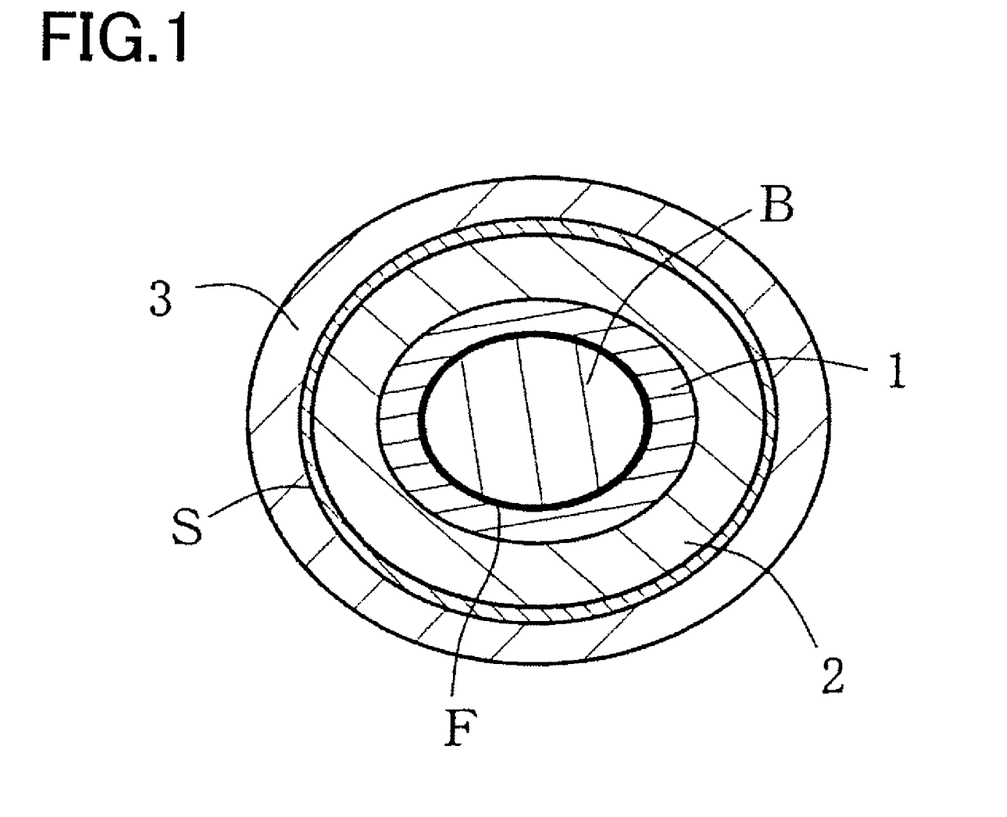
FIG. 1 is a cross-sectional view schematically illustrating an example of a bone strengthening food supplement.

FIG. 1 illustrates an example of a bone strengthening food supplement according to the present invention. This bone strengthening food supplement is produced in the form of mamegashi made by coating each black bean (black soybean) B with a plurality of layers having different compositions. Each of the black beans B is approximately spherical, and has an outer diameter of about 10 mm to about 20 mm.

A large number of pieces of the bone strengthening food supplement are included in a package so that an appropriate amount of calcium can be easily taken on the basis of number of pieces, according to the guideline indicated on the package. To enable an easier intake of calcium in a more appropriate manner, a given number of pieces of the bone strengthening food supplement required for one day may be included in each package, for example.

The black beans B, as a type of soybeans, are rich in isoflavone, which effectively reduces osteoporosis. The color of the black beans B is derived from anthocyanin-based pigment included in the seed coat. In this embodiment, the black beans B are neither ground nor subjected to such processes, to maintain their shape, and are used in the granular form. Although the black beans B are employed in this embodiment, general soybeans or other colored soybeans, e.g., yellow soybeans and green soybeans, may be employed, instead.

The black beans B are coated with a mineral layer 1 (a first layer) containing calcium powder and dolomite powder respectively having given proportions and also containing a binder, such as syrup, for binding these powders. A cereal flour layer F is interposed between the black beans B and the mineral layer 1 so as to stabilize formation of the mineral layer 1.

The calcium powder is made of inorganic calcium such as calcium carbonate. Materials for the calcium powder are not specifically limited, and may be egg shells, beef bones, or fish bones, for example. In this embodiment, powder of oyster shells subjected to a given process for food use is employed. Calcium powder obtained from oyster shells is superior because this type of calcium powder contains traces of marine minerals, in addition to calcium. The dolomite powder is obtained by processing dolomite, as a mineral, into a powdery form for food use, and originally contains calcium and magnesium in a relatively balanced manner.

As generally known, calcium and magnesium are preferably mixed such that one part by weight of magnesium is mixed with two parts by weight of calcium, in terms of the mineral balance. Thus, in this embodiment, the dolomite powder and calcium powder are mixed in such proportions that the ratio between calcium and magnesium in the total amount after mixture of all the materials is approximately 2:1.

Specifically, from 2 to 5 parts by weight of calcium powder and from 30 to 45 parts by weight of dolomite powder are mixed in 30 parts by weight of black beans.

If the proportions of the calcium powder and the dolomite powder deviated from the above-mentioned range, the mineral balance would be disturbed, resulting in difficulty in obtaining satisfactory mineral balance and satisfactory flavor at the same time even with adjustment of the proportions with respect to other materials. In addition, if the proportions of the calcium powder and the dolomite powder with respect to the black beans were higher than the above-mentioned range, the mineral layer 1 would become too thick, resulting in discomfort in resistance to teeth and flavor during chewing.

The mixture in the manner described above provides synergy effects of isoflavone, a large amount of which is contained in the black beans B, and well-balanced calcium and magnesium, thereby improving the balance of bone metabolism and promoting absorption of calcium.

The mineral layer 1 is covered with a dough layer 2 (a second layer) obtained by roasting a dough mixture including flour or kanbai-ko, for example. This dough layer 2 also contains a binder, such as syrup, for binding flour as mentioned above. The dough layer 2 has relatively soft and brittle properties because of expansion by roasting. Thus, these properties provide crispy texture during chewing, and in addition, make the supplement easy to chew for elderly people, for example.

The dough layer 2 is covered with a starch layer S. This starch layer S is provided in order to stabilize formation of an outside layer 3 (a third layer) formed on the outside of the starch layer S.

The outside layer 3 is the outermost layer of the bone strengthening food supplement, and is obtained by solidifying, with hardened fat or oil, a seasoning mixture including milk powder, such as soymilk powder, whole milk powder, and skim milk powder, and strong testing powder of tea and/or lemon peel (citrus calcium). This seasoning mixture may include powdery CPP in order to enhance absorption of calcium. As a material for promoting calcium absorption, materials except for CPP, e.g., fructo-oligosaccharide, calcium citrate-malate, poly glutamic acid, calcium hydrogenphosphate, phosphoryl oligosaccharide calcium, dibasic calcium phosphate, and casein phosphopeptide—amorphous calcium phosphate (CPP-ACP), may be used.

The soymilk powder is water-soluble powder obtained by processing soymilk, and is rich in isoflavone, which effectively reduces osteoporosis. The milk powder is water-soluble powder obtained by processing milk, and contains a relatively large amount of calcium, as well as has mild flavor. Thus, the milk powder also functions as a source of calcium, as an alternative to calcium powder, and in addition, contains lactose, which enhances absorption of calcium, thereby further increasing bone density.

Specifically, from 5 to 15 parts by weight of soymilk powder and from 10 to 40 parts by weight of milk powder are preferably mixed in 30 parts by weight of black beans.

Then, the resultant supplement shows a mineral balance with which calcium is easily absorbed as a whole, has good flavor, and is allowed to have an outside layer with an appropriate thickness, while reducing stickiness due to moisture absorption in the materials.

Powdered tea, which is astringent and bitter, matches well with flavors of the calcium powder and the dolomite powder, and thus can effectively mask these strong flavors. In addition, since powdered tea is rich in catechin, advantages of, for example, controlling a blood-pressure rise and adjusting blood glucose levels can be obtained.

Specifically, from 20 to 40 parts by weight of powdered tea are preferably mixed in 30 parts by weight of black beans. Then, a sufficient masking effect can be obtained, and in addition, other hygroscopic materials can be uniformly dispersed with ease in mass production, thereby enhancing workability.

The lemon peel is rich in calcium, and can be used as a source of calcium. Thus, the lemon peel can substitute for part of the calcium powder. In addition, sour taste unique to the lemon peel can effectively mask the taste of the calcium powder, for example.

Specifically, from 10 to 30 parts by weight of lemon peel powder are preferably mixed in 30 parts by weight of black beans. In addition to the lemon peel powder, powder of lemon flesh may be mixed. In this case, the flavor of lemon flesh can improve the taste of the supplement. Instead of, or in addition to, lemon, other citruses containing large amounts of calcium, such as Yuzu and Sudachi, may be used.

The material, CPP, is widely used to promote absorption of calcium. In this embodiment, from 1 to 4 parts by weight of CPP powder are preferably mixed in 30 parts by weight of black beans. Then, when combined with hardened fat or oil, CPP is effectively dispersed to efficiently perform its function. In contrast, if the proportion of CPP were higher than the above-mentioned range, CPP would absorb more moisture to be sticky, thereby reducing workability in mass production.

The hardened fat or oil is hardened at room temperature. In this embodiment, hydrogenated fat or oil of soybeans is employed. The melting point of the hardened fat or oil is preferably 40° C. to 50° C. because melting points of 50° C. or higher would cause problems in masking and easiness of eating.

Specifically, since the outside layer 3 is formed by solidifying a powdery seasoning mixture with this hardened fat or oil, the outside layer 3 can maintain an appropriate hardness even though the outside layer 3 is relatively thick. Thus, a combination of the outside layer 3 with the dough layer 2 can obtain a good texture. Accordingly, even elderly people, for example, can crush the black beans B and the mineral layer 1 at a time by chewing, without feeling discomfort.

Further, when the supplement is placed in the mouth, hardened fat or oil is softened by heat of the body, thereby causing the seasoning mixture such as powdered tea to melt. Consequently, the flavor of the mineral layer 1 is more effectively masked, thereby improving the taste. In addition, since the hardened fat or oil can prevent moisture absorption in the mineral layer 1 and the dough layer 2, the texture of the supplement can be stably maintained, and mixture with milk powder or CPP having a relatively high hygroscopicity does not make the supplement sticky and easy to carry.

Figure 2:
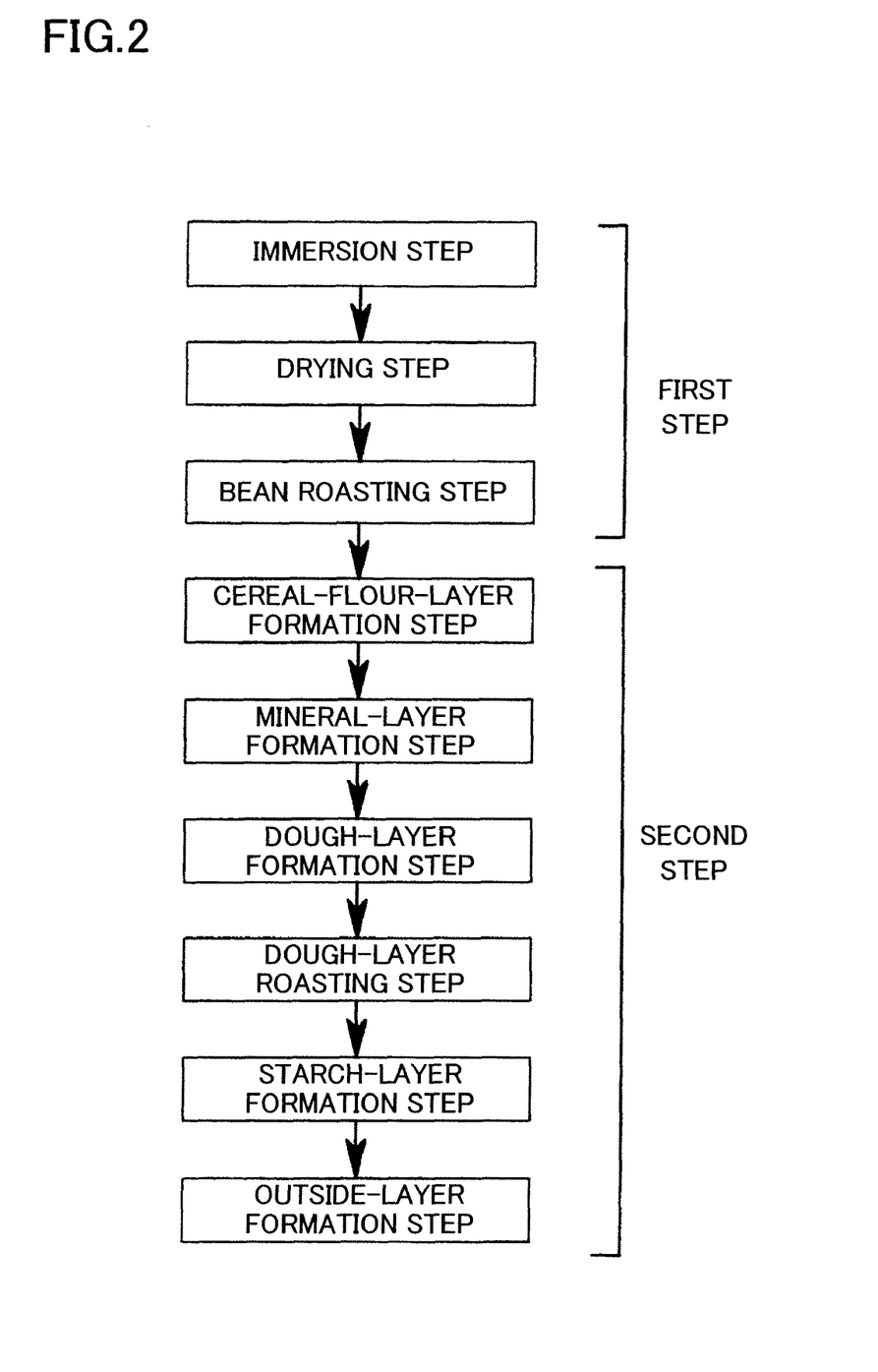
FIG. 2 is a flow chart showing process steps of producing a bone strengthening food supplement.

Then, a method for producing the bone strengthening food supplement of this embodiment will be described with reference to a flow chart shown in FIG. 2. As shown in FIG. 2, the process of producing the bone strengthening food supplement is divided into a first step and a second step in order to enhance workability and productivity. Each of the steps is designed to be processed in a batch.

In the first step, roasted black beans B to be cores of respective pieces of the bone strengthening food supplement are formed.

Specifically, first, raw black beans B are immersed in water for 5 to 15 hours to swell with conditions adjusted as necessary in consideration of, for example, the water temperature (an immersion step). Next, to remove redundant moisture, the immersed black beans B are taken out, and warm air is blown to the black beans B to dry the surfaces thereof (a drying step). Then, the black beans B which have swelled and softened are roasted with a drum-type roaster (a bean roasting step). The roasting is performed at a temperature of 140° C. to 200° C. for 10 minutes to 30 minutes, for example. The roasting conditions can be adjusted as necessary in the above-mentioned ranges to obtain preferred flavor.

In the second step, the roasted black beans B are covered with a plurality of layers.

Specifically, first, the black beans B roasted with the drum-type dedicated unit are subjected to powdering, thereby forming a mineral layer 1 and a dough layer 2.

Since it is difficult to stably form the mineral layer 1 directly on the roasted black beans B with stability, a cereal flour layer F is formed so as to cover the entire surface of the black beans B, before formation of the mineral layer 1 (a cereal-flour-layer formation step). This step enables stable formation of a given mineral layer 1 on each of the black beans B. The cereal flour may be wheat flour, rice flour, or buckwheat flour, for example. In this embodiment, wheat flour is employed.

Thereafter, a mixture of given proportions of calcium powder and dolomite powder is gradually added, with syrup, to the black beans B coated with the cereal flour layer F, thereby forming a mineral layer 1 on the surfaces of the black beans B (a mineral-layer formation step). Subsequently, a dough mixture including flour or kanbai-ko is added in the same manner, thereby forming a dough layer 2 on the outside of the mineral layer 1 (a dough-layer formation step).

After the formation of the dough layer 2, the black beans B are roasted with a fluidized roaster (a dough-layer roasting step). The use of the fluidized roaster for roasting with circulating hot air enables uniform heating of the dough layers 2 formed on the respective black beans B even in the case of processing a large amount of the black beans B, thereby allowing mass production while keeping stable quality. In this case, the roasting is performed at 150° C. to 200° C. for 10 minutes to 30 minutes, for example.

After the roasting of the dough layer 2, the black beans B are cooled to room temperature, and a starch layer S is formed on the surfaces of the black beans B (a starch-layer formation step). This starch layer S is intended for stable formation of an outside layer 3 to be formed next, and can be formed to cover the entire surface of the dough layer 2.

Then, the outside of the starch layer S is subjected to powdering using a seasoning mixture obtained by uniformly mixing given proportions of powdered tea, milk powder, and soymilk powder, for example, beforehand and also using solid oil or fat which has been changed into liquid by heating, thereby forming an outside layer 3 (an outside-layer formation step).

If the outside layer 3 were formed directly on the surface of the dough layer 2, this formation of the outside layer 3 would be unstable. However, the starch layer S allows the outside layer 3 to be uniformly formed as a whole. At this time, soymilk powder, milk powder, and CPP having relatively high hygroscopicity are likely to form agglomeration. However, mixture with powdered tea and/or lemon peel powder enables the above materials to be uniformly dispersed with ease, thereby allowing proportions of the materials to be uniform among the beans.

The resultant bone strengthening food supplement thus produced is easy to eat, and in addition, has an optimum mineral balance, e.g., about 4200 mg of calcium and about 2100 mg of magnesium per 100 g of the supplement, thereby enabling an easy intake of a necessary amount of calcium in a balanced manner as needed.

EXAMPLES

Figure 3:
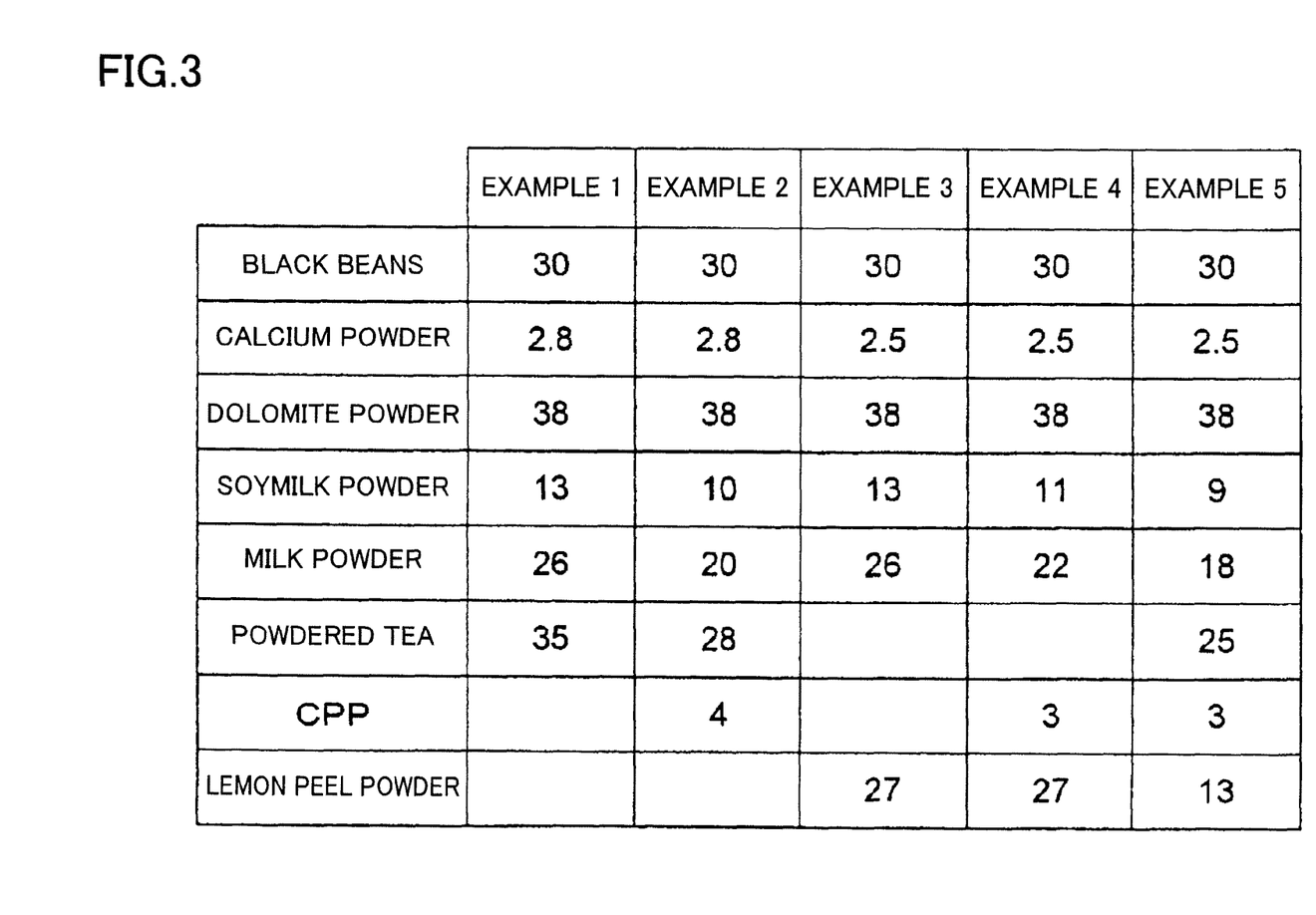
FIG. 3 is a table showing examples of the bone strengthening food supplement.

FIG. 3 shows Examples 1 through 5 of the bone strengthening food supplement of the present invention. Example 1 is obtained by adding powdered tea to a basic mixture of calcium powder, dolomite powder, and soymilk powder, for example. Example 2 is obtained by adding CPP to the basic mixture in addition to powdered tea. Example 3 is obtained by adding lemon peel powder, instead of powdered tea, to the basic mixture so as to substitute the lemon peel powder for part of the calcium powder. Example 4 is obtained by adding lemon peel powder to the basic mixture so as to substitute the lemon peel powder for part of the calcium powder, in addition to CPP. Example 5 is obtained by further adding powdered tea to the basic mixture so as to adjust flavor. The values shown in the table of FIG. 3 are expressed in parts by weight.

Tasting of the bone strengthening food supplements of Examples 1 through 5 showed that all the supplements did not have flavor of calcium powder and dolomite powder, and tasted well with favorable texture. In addition, the supplements showed an excellent mineral balance in which the ratio between calcium and magnesium was approximately 2:1.
(Verification Experiment)

A verification experiment was conducted to verify an influence of the bone strengthening food supplement on bone density by using 18-week-old adult mice. In this experiment, normal male/female mice and gonadectomized mice (also called osteoporosis model mice) from which gonads (testes or ovaries) have been removed in order to forcedly cause osteoporosis were used.

The diets for the mice were: a powdery food containing 0.9% of Ca and satisfying a recommended calcium intake (produced by CREA Japan, Inc., and also referred to as a recommended Ca food); a powdery food containing 0.63% of Ca and reproducing a Ca-intake deficiency based on the result of the national health and nutrition survey, 2003 (produced by CREA Japan, Inc., and also referred to as a Ca-deficient food); and pulverized pieces of the bone strengthening food supplements of Examples 1 and 2 (also referred to as an Example 1 food and an Example 2 food, respectively).

In the experiment, the mice were divided into groups: a group (group A) of normal mice fed the recommended Ca food; a group (group B) of normal mice fed the Ca-deficient food; a group (group C) of normal mice fed a food obtained by adding the Example 1 food to the Ca-deficient food so as to satisfy the recommended calcium intake; a group (group D) of osteoporosis model mice fed the Ca-deficient food; a group (group E) of osteoporosis model mice fed a food obtained by adding the Example 1 food to the Ca-deficient food so as to satisfy the recommended calcium intake; and a group (group F) of osteoporosis model mice fed a food obtained by adding the Example 2 food to the Ca-deficient food so as to satisfy the recommended calcium intake. These groups of mice were grown up under given conditions, and then the bone densities and the bone mineral densities in cancellous bones and cortical bones of femora were measured with a bone-density measurement system (where n=60).

Figure 4A:
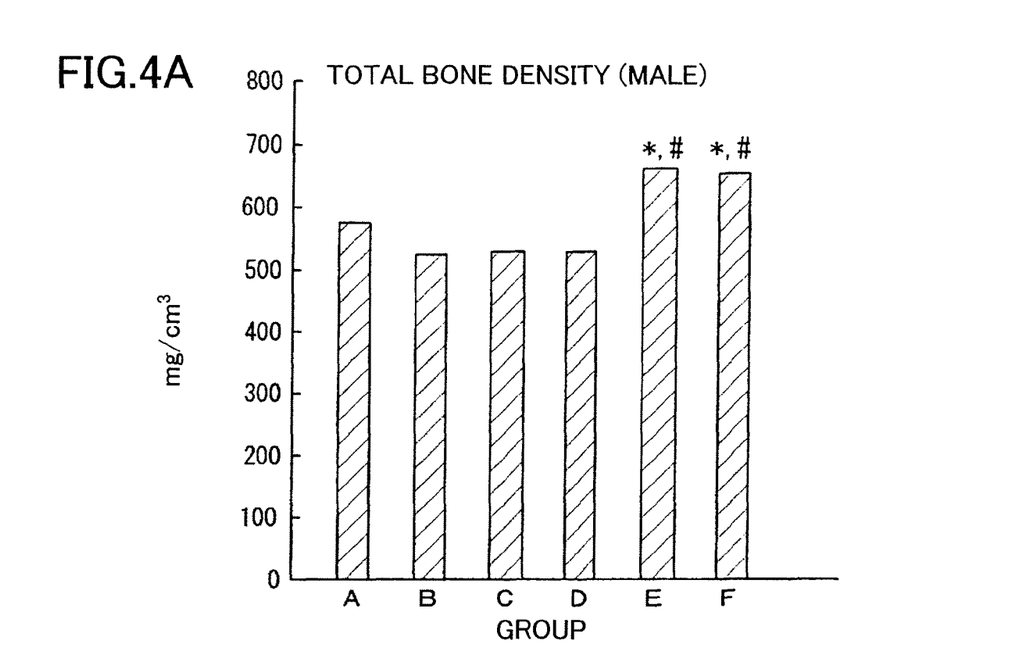
FIG. 4(a) shows the total bone densities.
Figure 4B:
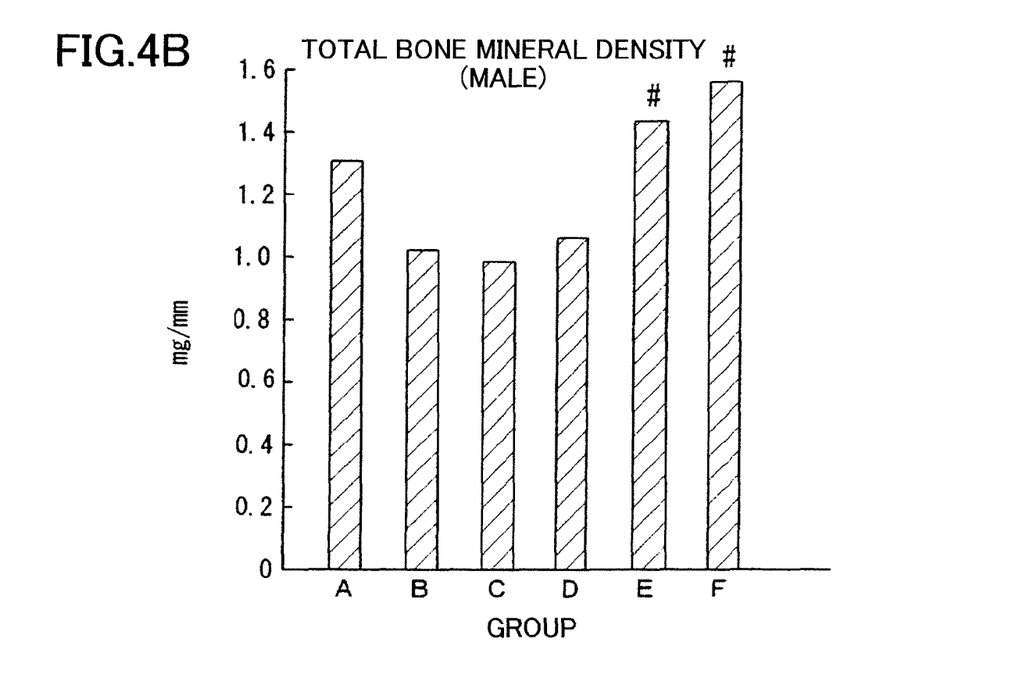
FIG. 4(b) shows the total bone mineral densities.
Figure 5A:
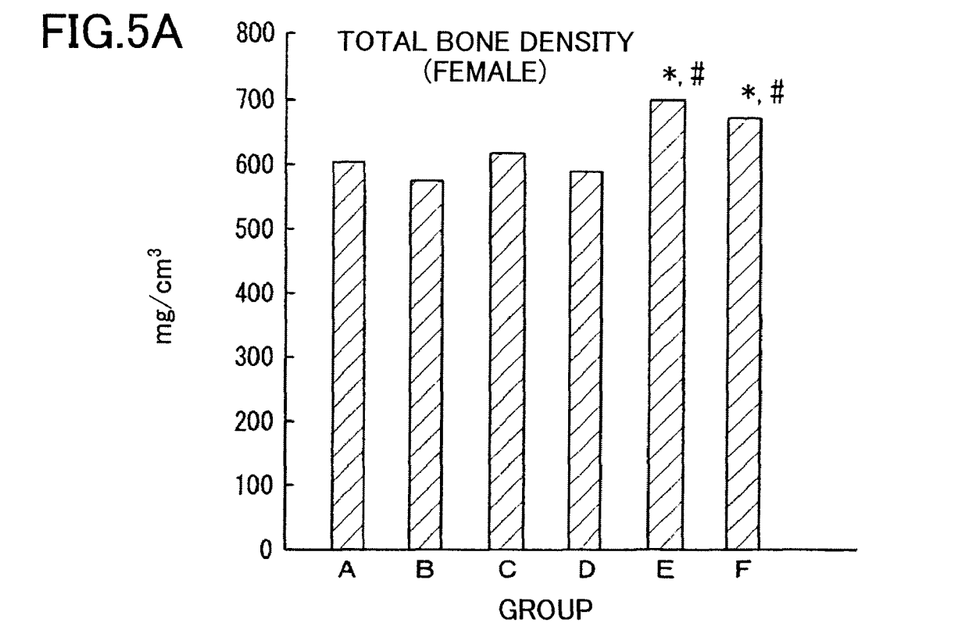
FIG. 5(a) shows the total bone densities.
Figure 5B:
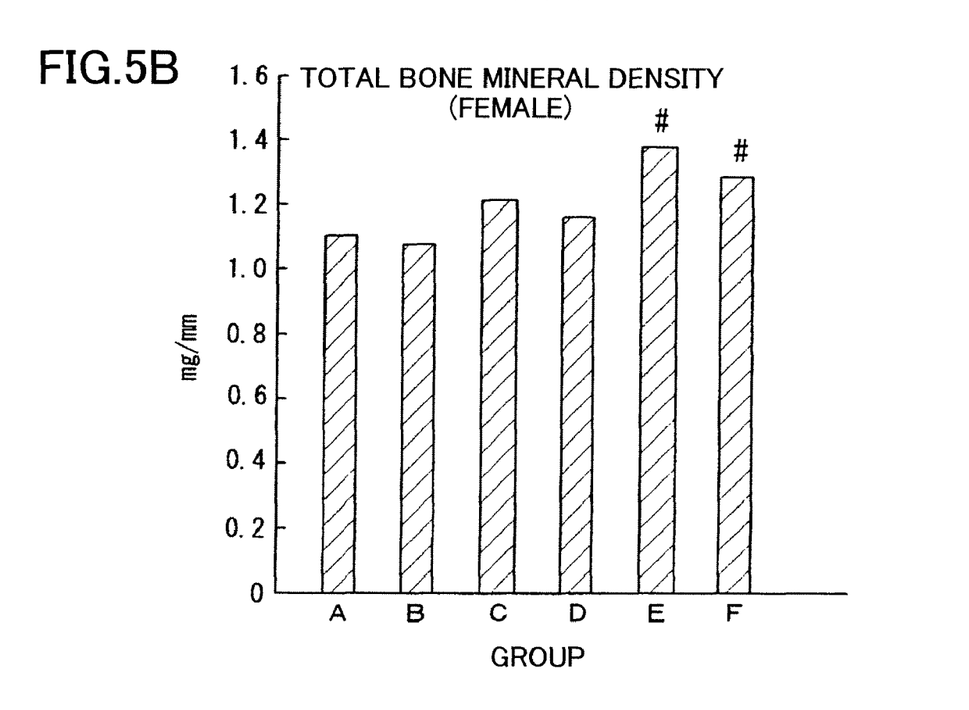
FIG. 5(b) shows the total bone mineral densities.
Figure 6A:
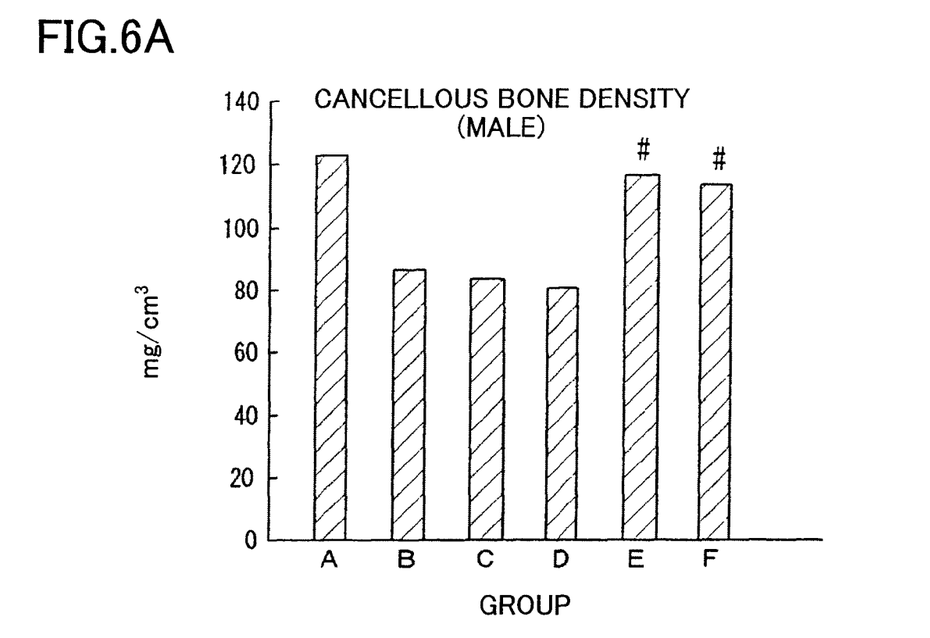
FIG. 6(a) shows the cancellous bone densities.
Figure 6B:
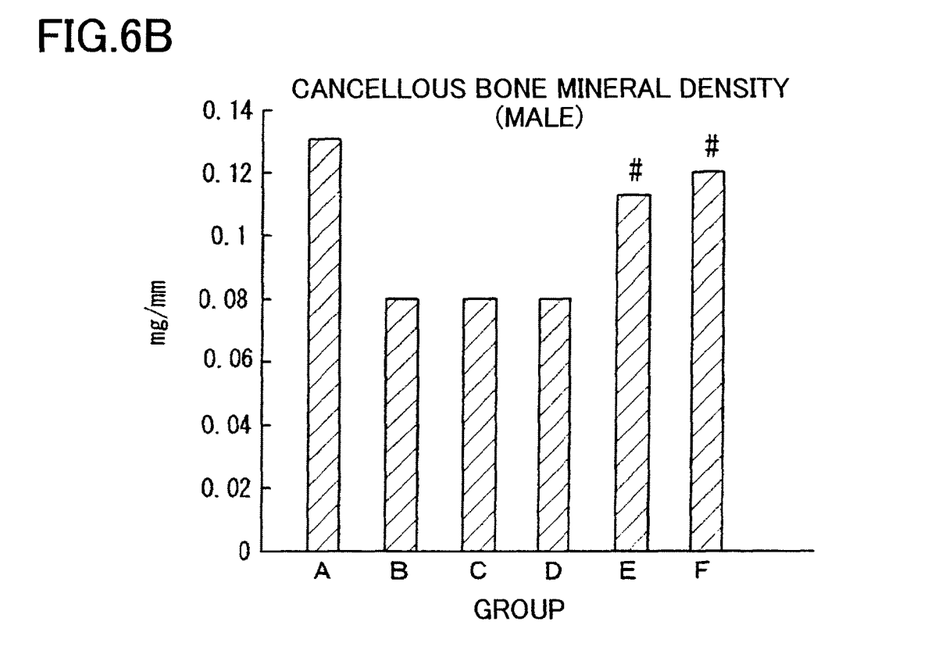
FIG. 6(b) shows the cancellous bone mineral densities.
Figure 7A:
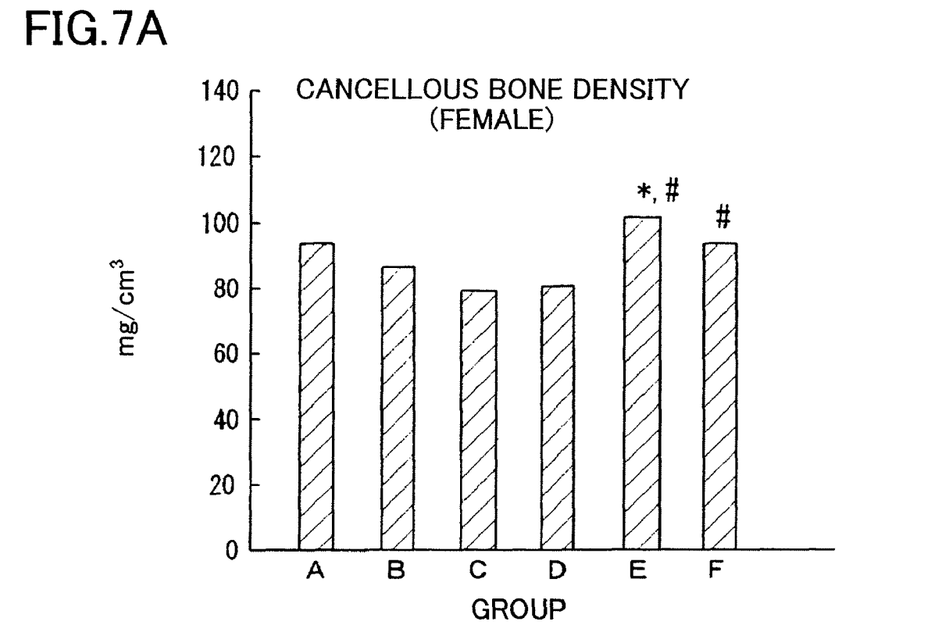
FIG. 7(a) shows the cancellous bone densities.
Figure 7B:
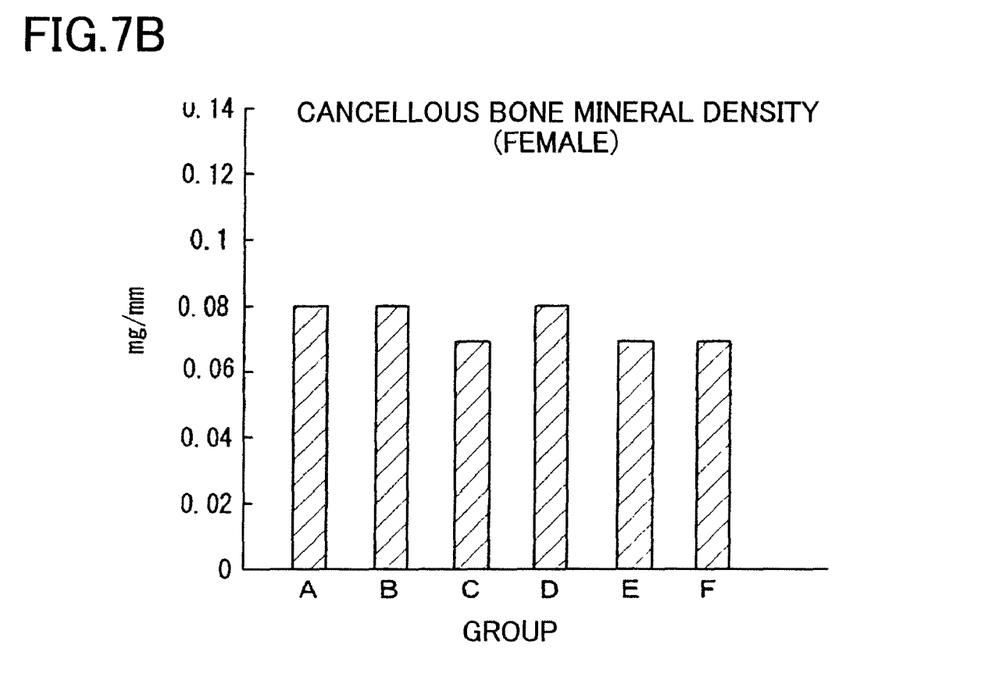
FIG. 7(b) shows the cancellous bone mineral densities.
Figure 8A:
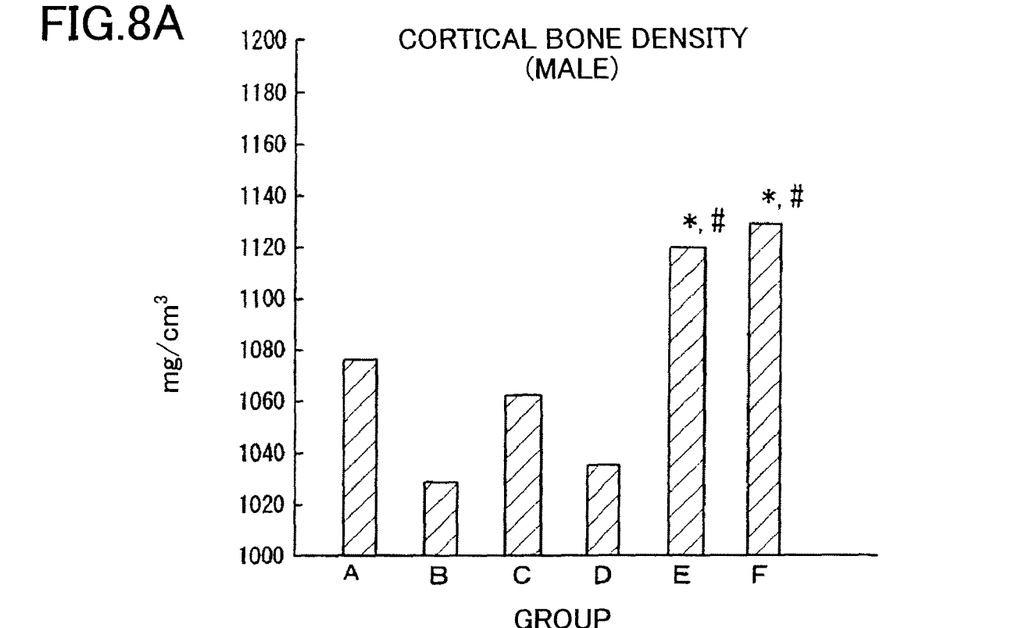
FIG. 8(a) shows the cortical bone densities.
Figure 8B:
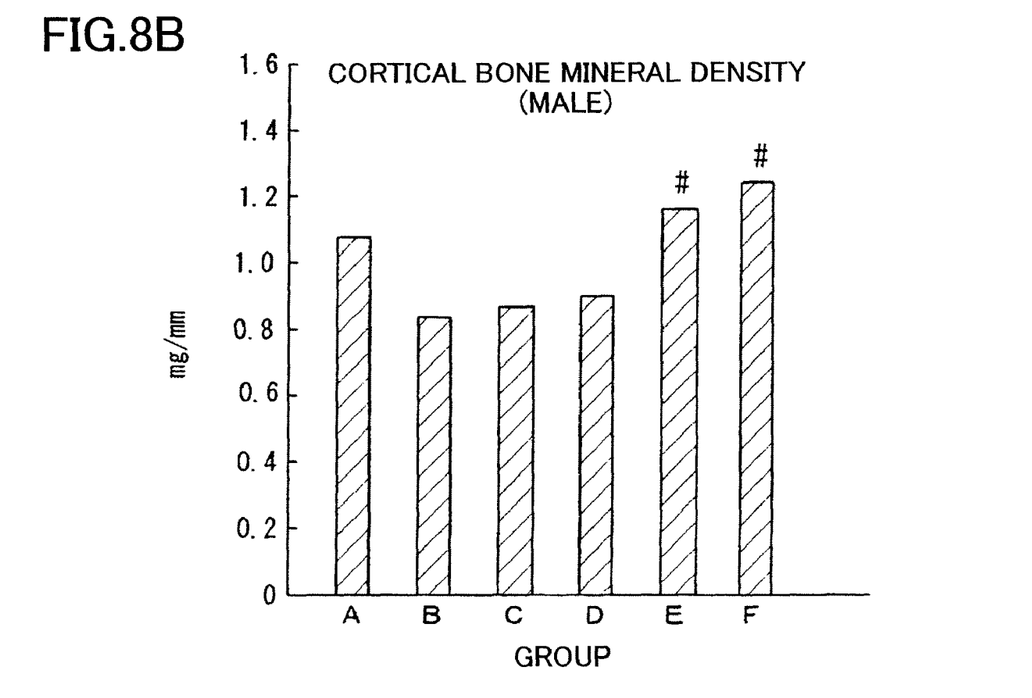
FIG. 8(b) shows the cortical bone mineral densities.
Figure 9A:
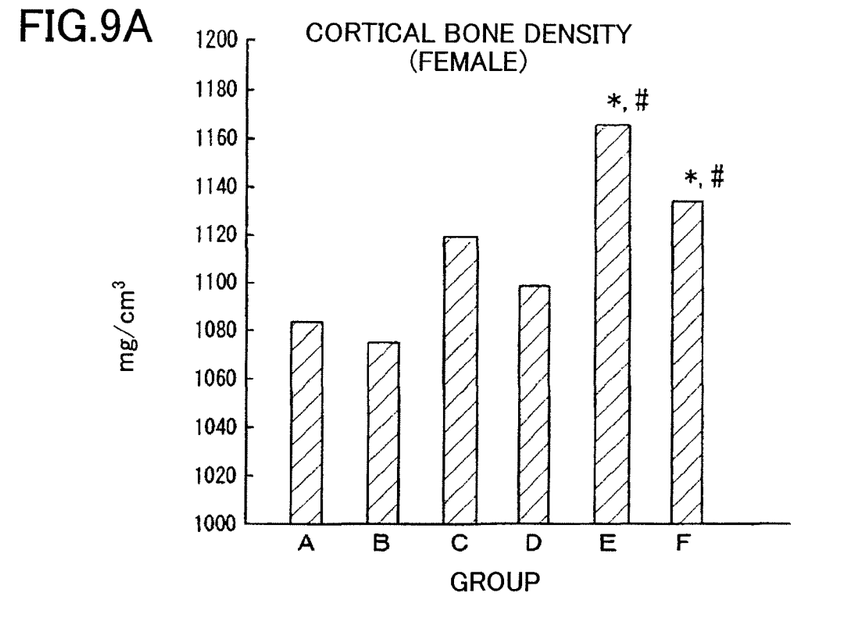
FIG. 9(a) shows the cortical bone densities.
Figure 9B:
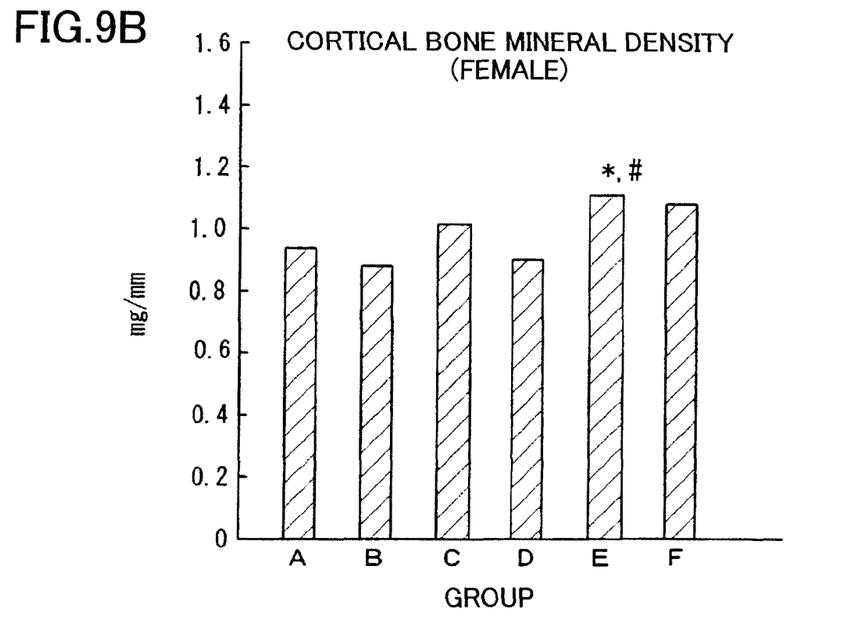
FIG. 9(b) shows the cortical bone mineral densities.

FIGS. 4 through 9 show results of the measurement. Specifically, FIGS. 4 and 5 show results of measurements of the total bone densities and the total bone mineral densities in male mice and female mice. FIGS. 6 and 7 show results of measurements of the cancellous bone densities and the cancellous bone mineral densities in the same manner. FIGS. 8 and 9 show results of measurements of the cortical bone densities and the cortical bone mineral densities in the same manner. In each graph of the drawings, the symbol "*" means significant (where $p<0.05$) as compared to group A, and the symbol "#" means significant (where $p<0.05$) as compared to group D.

As shown in graphs (a), the bone densities of groups E and F of mice in which osteoporosis has forcedly been caused and which were fed the Example 1 food or the Example 2 food, increase for both of the cancellous bones and the cortical bones, as shown in FIGS. 6 through 9. In particular, the bone densities in the cortical bones remarkably increase, and significantly increase as compared to groups A and D.

As a result, as shown in FIGS. 4 and 5, the total bone densities increase more greatly than those in the other groups in each of the cases of male mice and female mice. Although the degree of increase does not reach those in groups E and F, the bone densities in group C of normal mice fed the Example 1 food are generally higher than those in group B not fed the Example 1 food.

As shown in graphs (b), the bone mineral densities show almost the same results as those for the bone densities, and significantly increase especially in groups E and F in general.

The above verification experiment was performed by using mice. However, the same results were also observed in human. For example, the bone mass of elderly people having 93.1% of the average bone mass of people of the same age, was increased to 98.9% by a continuous daily intake of a given amount of the bone strengthening food supplement for six months. In the same manner, 78% of the bone mass of elderly people was increased to 82% in four months.

Accordingly, the bone strengthening food supplement of the present invention can increase bone density, and especially improve osteoporosis. In addition, the supplement can be continuously taken with ease, as snacks are, and thus are highly effective in eliminating calcium deficiency The bone strengthening food supplement of the present invention is not limited to the foregoing embodiment, and includes other variations. For example, the supplement is in the form of mamegashi in the above embodiment, but may be formed in blocks, i.e., in the form of pastry, or in a powdery form. Alternatively, for use as a liquid food, for example, the supplement may be formed by adding water to powdered materials to obtain a liquid or gelled form.

DESCRIPTION OF REFERENCE CHARACTERS 1 mineral layer (first layer)
2 dough layer (second layer)
3 outside layer (third layer)
B black bean (soybean)
F cereal flour layer
S starch layer

The invention claimed is:

1. A bone strengthening food supplement which is approximately spherical, the bone strengthening food supplement comprising:
    soybeans which were immersed in water to swell and then were roasted;
    a starch layer covering a surface of each of the soybeans;
    a first layer containing calcium powder and dolomite powder and covering a surface of the starch layer;
    a second layer which has expanded by roasting a dough mixture containing flour, and covers a surface of the first layer;
    a starch layer covering a surface of the second layer; and
    a third layer containing hardened fat or oil and covering a surface of the starch layer, the hardened fat or oil containing unfermented soymilk powder and having a melting point of 40° C. to 50° C., wherein
    an amount of the calcium powder is from 2 to 5, both inclusive, parts by weight per 30 parts by weight of the soybeans,
    an amount of the dolomite powder is from 30 to 45, both inclusive, parts by weight per 30 parts by weight of the soybeans, and
    an amount of the soymilk powder is from 5 to 15, both inclusive, parts by weight per 30 parts by weight of the soybeans.

2. The bone strengthening food supplement of claim 1, further comprising lactose-containing milk powder, wherein
    an amount of the milk powder is from 10 to 40, both inclusive, parts by weight per 30 parts by weight of the soybeans.

3. The bone strengthening food supplement of claim 1, further comprising powdered tea.

4. The bone strengthening food supplement of claim 1, further comprising wherein at least part of the calcium powder comprises citrus calcium.

5. The bone strengthening food supplement of claim 1, further comprising casein phosphopeptide, wherein
    an amount of the casein phosphopeptide is from 1 to 4, both inclusive, parts by weight per 30 parts by weight of the soybeans.

6. The bone strengthening food supplement of claim 1, further comprising at least one material selected from the group consisting of fructo-oligosaccharide, calcium citratemalate, poly glutamic acid, calcium hydrogenphosphate, phosphoryl oligosaccharide calcium, dibasic calcium phosphate, and casein phosphopeptide—amorphous calcium phosphate.

* * * * *